United States Patent [19]

Watanabe

[11] Patent Number: 5,448,988
[45] Date of Patent: Sep. 12, 1995

[54] ENDOSCOPE

[75] Inventor: Izumi Watanabe, Tochigiken, Japan

[73] Assignee: Kabushiki Kaisha Toshiba, Kawasaki, Japan

[21] Appl. No.: 159,582

[22] Filed: Dec. 1, 1993

[30] Foreign Application Priority Data

Dec. 2, 1992 [JP] Japan .................. 4-323238

[51] Int. Cl.6 .................................... A61B 1/00
[52] U.S. Cl. .................... 600/139; 138/118; 600/112
[58] Field of Search ............... 138/DIG. 7, 118, 137, 138/141; 128/4, 6; 604/282, 280

[56] References Cited

U.S. PATENT DOCUMENTS

| | | | |
|---|---|---|---|
| 4,279,245 | 6/1981 | Takagi et al. | 128/4 |
| 4,753,222 | 6/1988 | Morishita | 128/4 |
| 4,899,787 | 2/1990 | Ouchi et al. | 138/131 |
| 5,217,002 | 6/1993 | Katsurada et al. | 128/4 |

Primary Examiner—Richard J. Apley
Assistant Examiner—Beverly M. Flanagan
Attorney, Agent, or Firm—Foley & Lardner

[57] ABSTRACT

An endoscope has a flexible tube covered with a covering layer. The covering layer is made from polyester-based soft thermoplastic elastomer containing hard segments of liquid crystal monomers and polyester-based hard thermoplastic elastomer containing hard segments of PBT.

11 Claims, 3 Drawing Sheets

ENDOSCOPE

BACKGROUND OF THE INVENTION

1. Field of the Invention

The present invention relates to a flexible tube of an endoscope, and particularly, to a durable and heat resistant covering layer of the flexible tube.

2. Description of the Prior Art

An endoscope is a medical apparatus inserted into a patient's body cavity. The endoscope has a photographing unit to pick up images inside the patient. The images are displayed on a display and are used for diagnosis.

FIG. 1 shows an example of an endoscope. The endoscope has a controller 1 and an inserter 4 to be inserted into a patient's body cavity. The inserter 4 has a flexible tube 2 and a bending portion 3. The angle of the bending portion 3 is adjustable through the controller 1.

FIG. 2 is a longitudinal section showing the flexible tube 2. The flexible tube 2 has a spiral metal flex 8, a braid 7 of stainless steel wires wound around the flex 8, and a covering layer 6 covering the braid 7. The covering layer 6 is a lamination of layers of rubber and urethane-based thermoplastic elastomer.

The flexible tube 2 must be flexible to enter a patient's body cavity and must be hard to transfer insertion force to the leading end thereof. To provide the flexibility and bending rigidity to the flexible tube 2, a conventional endoscope forms the covering layer 6 with a lamination of layers of dissimilar materials. Due to the dissimilarity, the layers insufficiently adhere to one another and peel off after extended use of the endoscope, thereby deteriorating the insertion ability and appearance of the endoscope.

When the covering layer 6 is partly formed from the urethane-based thermoplastic elastomer, it demonstrates poor heat resistance and softens when it is used at high temperatures or after high-temperature sterilization. This results in deteriorating the insertion ability of the endoscope. In addition, the urethane-based thermoplastic elastomer causes hydrolysis and reduces the hardness of the flexible tube 2.

The urethane-based thermoplastic elastomer is too hard to form a soft part. Even if the soft part is made from the elastomer, the soft part must be laminated with a hard layer to provide bending rigidity. Such lamination complicates production processes and weakens durability in interlayer areas.

Alternatively, the flexible tube 2 may be made from hard segments of polybutylene terephthalate (PBT) and soft segments of polyester-based thermoplastic elastomer having aliphatic polyester or aliphatic polyether. These materials, however, provide insufficient softness and raise the same problem as the urethane-based thermoplastic elastomer.

SUMMARY OF THE INVENTION

To solve these problems, an object of the present invention is to provide an endoscope with a flexible tube having durability and flexibility.

In order to accomplish the object, the present invention provides an endoscope having a flexible tube and a photographing unit to be inserted into a patient's body cavity, to diagnose the inside of the patient. The flexible tube is covered with a covering layer made from at least two kinds of polyester-based thermoplastic elastomer each having a mixture of hard and soft segments. The hard segments of at least one of the two kinds of polyester-based thermoplastic elastomer are liquid crystal monomers.

The polyester-based thermoplastic elastomer having the hard segments of liquid crystal monomers forms a soft material, and the polyester-based thermoplastic elastomer having hard segments of PBT forms a hard material. These soft and hard materials are laminated one upon another or mixed with each other to form the covering layer of the flexible tube of the endoscope. Since the soft and hard materials are made from similar materials, the materials tightly adhere to each other, to provide the flexible tube with flexibility, heat resistance, and durability.

These and other objects, features and advantages of the present invention will be more apparent from the following detailed description of preferred embodiments in conjunction with the accompanying drawings.

DETAILED DESCRIPTION OF THE EMBODIMENTS

Figure 1:
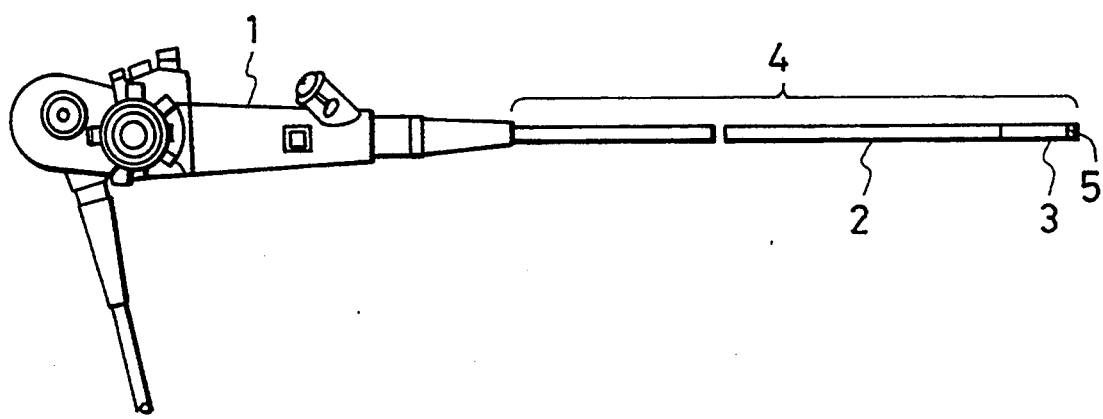
FIG. 1 shows an endoscope.
Figure 2:
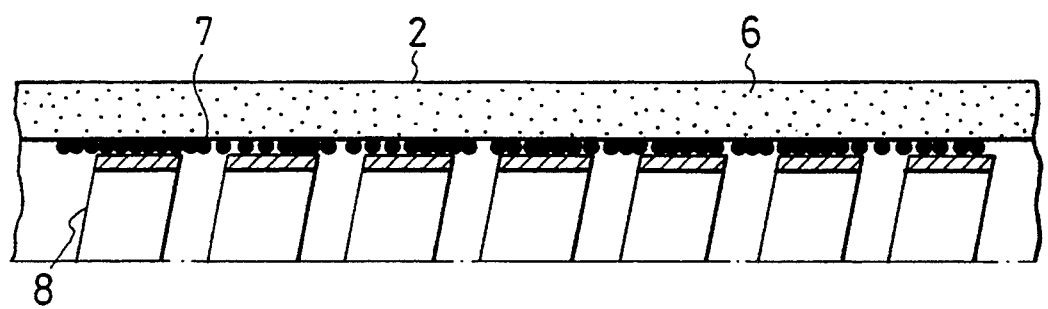
FIG. 2 is a longitudinal section showing a flexible tube of a conventional endoscope art.

The configuration of an endoscope according to the present invention is generally the same as the conventional one shown in FIg. 1. Namely, the endoscope according to the present invention has a controller 1 and an inserter 4 to be inserted into a patient's body cavity. The inserter 4 has a flexible tube 2 and a bending portion 3. The angle of the bending portion 3 is adjustable through the controller 1. At the end of the bending portion 3, an image sensing portion 5 comprising an Image sensor such as a CCD is provided.

Figure 3:
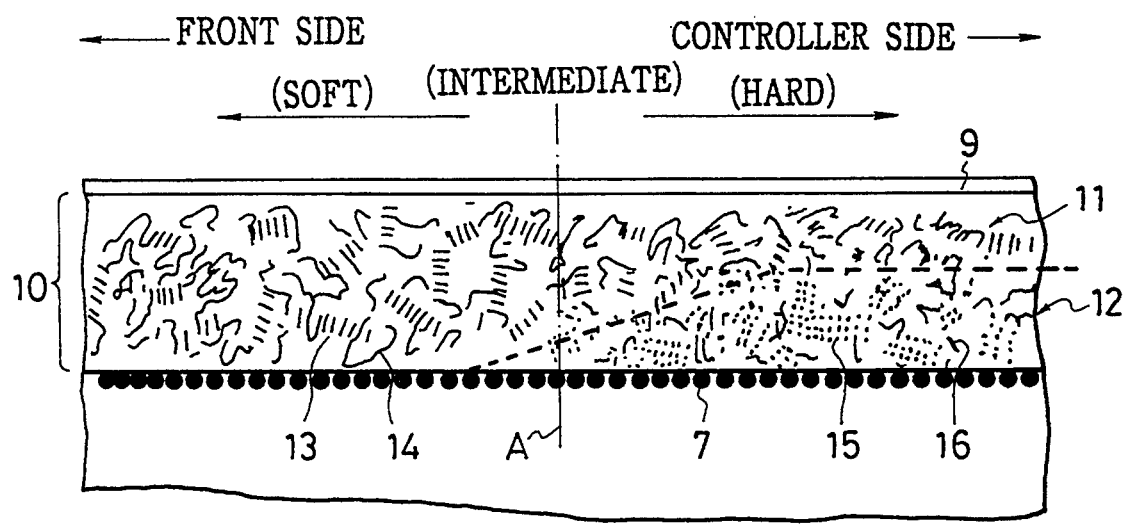
FIG. 3 is a longitudinal section showing a flexible tube of an endoscope according to a first embodiment of the present Invention.

FIG. 3 is a longitudinal section showing the flexible tube 2 of the endoscope, according to the first embodiment of the present invention. The flexible tube 2 has a braid 7 and a covering layer covering the braid 7.

The covering layer is made from a thermoplastic elastomer material 10 and a periphery 9. The elastomer material 10 includes a first elastomer material (soft elastomer) 11 that is soft and has high flexibility and a second elastomer material (hard elastomer) 12 that is hard and has low flexibility.

In FIG. 3, the flexible tube 2 In the vicinity of the bending portion 3 located on the front side of the endoscope is made of only the first elastomer material The thickness of the second elastomer material 12 gradually increases from a hardness changing intermediate position A toward the controller 1 located on the rear side of the endoscope. In the vicinity of the controller 1, the thicknesses of the first and second elastomer materials and 12 are substantially equal to each other.

In this way, the flexible tube 2 is soft and highly flexible in the vicinity of the bending portion 3 and becomes harder and lower in flexibility from the hardness changing position A toward the controller 1.

Figure 4:
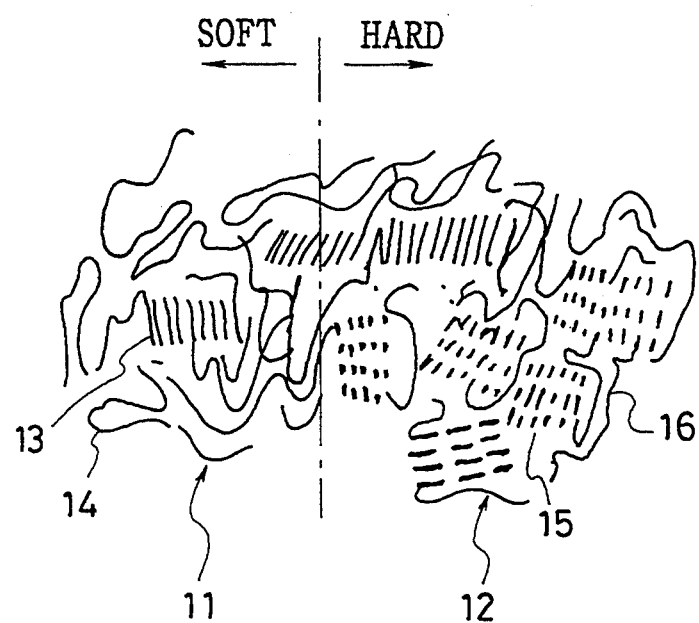
FIG. 4 shows first and second elastomer materials forming a covering layer of the flexible tube of FIG. 3.

FIG. 4 shows the first and second elastomer materials 11 and 12. The first elastomer material 11 has a mixture of hard segments 13 of liquid crystal monomers and soft segments 14 of polyester-based elastomer having aliphatic polyester. The second elastomer material 12 has a mixture of hard segments 15 of PBT and soft segments of polyester-based elastomer having aliphatic polyester.

Namely, the first and second elastomer materials 11 and 12 have the soft segments of aliphatic polyester of the same kind. Accordingly, the elastomer materials 11 and 12 have good compatibility and adhesion and hardly peel off.

The polyester-based thermoplastic elastomer has good heat resistance, and therefore, the flexibility of the flexible tube 2 is not affected by high-temperature sterilization at 100 to 120 degrees centigrade.

The periphery 9 (FIG. 8) may be made of one of the first and second elastomer materials 11 and 12 according to the application of the flexible tube 2.

Although the above embodiment employs a two-layer structure of two kinds of elastomer, this arrangement does not limit the present Invention. The present invention may employ a multilayer structure of various kinds of elastomer.

Figure 5:
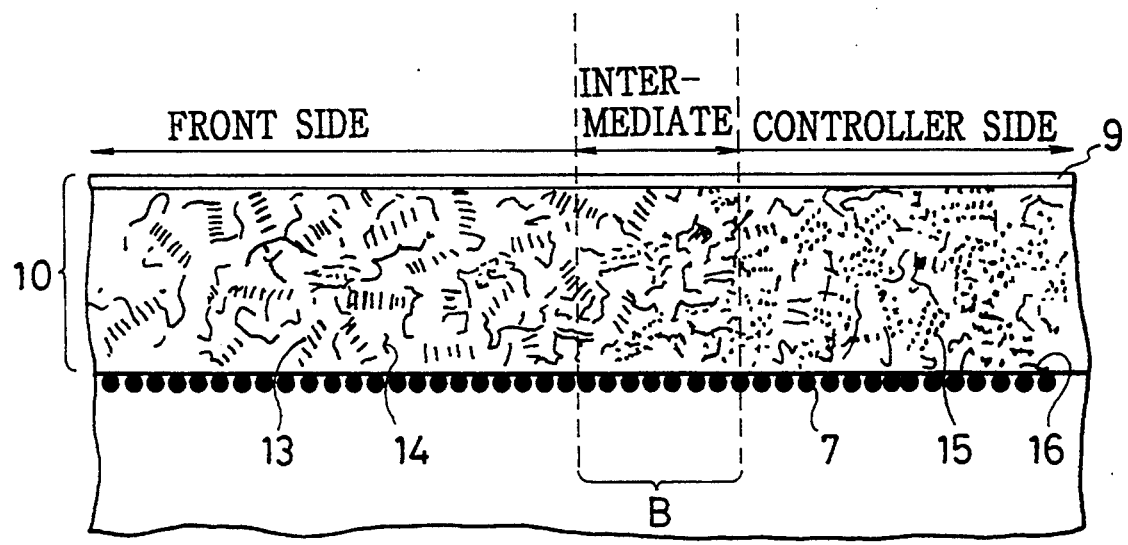
FIG. 5 is a longitudinal section showing a flexible tube of an endoscope according to a second embodiment of the present invention.

FIG. 5 is a longitudinal section showing a flexible tube 2 of an endoscope according to the second embodiment of the present invention. Unlike the first embodiment that laminates the two kinds of the elastomer materials 11 and 12 one upon another, the second embodiment mixes two kinds of elastomer materials at different mixing ratios to adjust flexibility.

Namely, the second embodiment employs a mixture of a first elastomer material 11 of polyester-based soft thermoplastic elastomer and a second elastomer material 12 of hard thermoplastic elastomer. The mixing ratio of the first and second elastomer materials 11 and 12 is changed from the center of an intermediate area B such that the quantity of the hard elastomer material 12 is increased from the intermediate area B toward the controller 1 located on the rear side of the endoscope, and the quantity of the soft elastomer material 11 is increased from the intermediate area B toward the bending portion 3 located on the front side of the endoscope.

Consequently, the flexible tube 2 has high flexibility in the vicinity of the bending portion 3 and low flexibility in the vicinity of the controller 1.

Due to this monolayer structure, the flexible tube 2 hardly peels off.

According to the second embodiment, the mixing ratio of the first and second elastomer materials 11 and 12 is gradually changed from the center of the intermediate area B. This does not limit the present invention. For example, the first and second elastomer materials 11 and 12 may be mixed with each other at quite different ratios on the opposite sides of a plane.

The intermediate position A of the first embodiment and the intermediate area B of the second embodiment may be optionally positioned on the flexible tube 2 according to the application of the endoscope. The position A and area B are usually positioned on the flexible tube 2 within 30 cm from the bending portion 3.

The polyester-based soft thermoplastic elastomer employable for the present invention may contain liquid crystal elastomer S-TPE of SEKISUI KAGAKU KOGYO. The polyester-based thermoplastic elastomer employable for the present invention may contain PERPLENE (a trade name) of TOYO BOSEKI, HITRAIL (a trade name) of DUPONT/TOYO PRODUCT, or ARNITEL (a trade name) of AKZO.

In summary, a covering layer of a flexible tube of an endoscope according to the present invention is made of soft and hard materials. The soft material contains soft segments of polyester-based thermoplastic elastomer and hard segments of liquid crystal monomers. Due to this structure, the flexible tube has high flexibility, compatibility, and adhesion, to hardly peel even after extended use. The flexible tube also has excellent heat resistance to prevent quality deterioration during high-temperature sterilization.

Various modifications will become possible for those skilled in the art after receiving the teachings of the present disclosure without departing from the scope thereof.

What is claimed is:

1. An endoscope having an insert part to be inserted into a patient and a control part connected to the insert part, said insert part comprising:
   a flexible portion having a covering layer provided on an outer surface of the flexible portion, wherein
   said covering layer includes a soft elastomer and a hard elastomer, the soft elastomer containing liquid crystal monomers, and
   each of the soft and hard elastomers is a mixture of hard segments and soft segments, the liquid crystal monomers serving as the hard segments of the soft elastomer.

2. The endoscope according to claim 1, wherein the soft segments contained in each of the soft and hard elastomers are of the same kind.

3. The endoscope according to claim 1, wherein each of the elastomers comprises polyester-based thermoplastic elastomer.

4. The endoscope according to claim 1, wherein said covering layer around a front end of the insert part is made from the soft elastomer containing the liquid crystal monomers.

5. The endoscope according to claim 1, wherein the soft elastomer contains hard segments of liquid crystal monomers and soft segments of aliphatic polyester, and the hard elastomer contains hard segments of polybutylene terephthalate and soft segments of allphatic polyester.

6. The endoscope according to claim 1, wherein a portion of said covering layer around a first longitudinal end of the insert part is made from the soft elastomer, and a portion of said covering layer around a second longitudinal end of the insert part is made from the soft and hard elastomers of substantially the same thickness, the thickness of the hard elastomer gradually increasing from a longitudinal center of the insert part toward the second longitudinal end.

7. The endoscope according to claim 1, wherein a portion of said covering layer around a first longitudinal end of the insert part is made from the soft elastomer, and a portion of said covering layer around a second longitudinal end of the insert part is made from the soft and hard elastomers, the soft and hard elastomers being mixed with each other in a longitudinal intermediate area of the insert part, the mixing ratio of the hard elastomer to the soft elastomer gradually increasing from the intermediate area toward the second longitudinal end.

8. The endoscope according to claim 1 wherein said covering layer is made from the soft elastomer near a first end of the insert part receiving light containing visual information and made from a dual layer composed of a soft elastomer layer and a hard elastomer layer at a second end of the insert part near the control part connected to the insert part.

9. The endoscope according to claim 8 wherein the ratio of the soft elastomer layer and the hard elastomer in the dual layer increases from a longitudinal intermediate position of the insert part to a position near the second end of the insert part.

10. The endoscope according to claim 1 wherein said covering layer is made from the soft elastomer near a first end of the insert part receiving light containing visual information and made from a mixture of the soft and hard elastomers at a second end of the insert part near the control part connected to the insert part.

11. The endoscope according to claim 10, wherein said covering layer is made from a mixture of the soft and hard elastomers near the center of the insert part, the mixing ratio of the hard elastomer to the soft elastomer near the second end of the insert part being greater than that at the center of the insert part.

* * * * *